(12) United States Patent
Ramzipoor et al.

(10) Patent No.: US 8,005,529 B2
(45) Date of Patent: Aug. 23, 2011

(54) SYSTEMS AND METHODS FOR INTERNAL TISSUE PENETRATION

(75) Inventors: Kamal Ramzipoor, Fremont, CA (US); James D. Koger, Santa Cruz, CA (US); Gopal Chopra, San Francisco, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 0 days.

(21) Appl. No.: 12/749,234

(22) Filed: Mar. 29, 2010

(65) Prior Publication Data

US 2010/0185054 A1 Jul. 22, 2010

Related U.S. Application Data

(63) Continuation of application No. 10/394,079, filed on Mar. 21, 2003, now Pat. No. 7,715,896.

(51) Int. Cl.
*A61B 5/05* (2006.01)
(52) U.S. Cl. ........ 600/407; 600/424; 600/437; 600/466; 600/462
(58) Field of Classification Search .................. 600/407, 600/437, 443, 459, 462, 466, 467, 473, 476, 600/101, 109, 112; 604/22
See application file for complete search history.

(56) References Cited

U.S. PATENT DOCUMENTS

| | | |
|---|---|---|
| 4,474,179 A | 10/1984 | Koch |
| 4,898,575 A | 2/1990 | Fischell et al. |
| 4,917,097 A | 4/1990 | Proudian et al. |
| 4,935,025 A | 6/1990 | Bundy et al. |
| 4,998,933 A | 3/1991 | Eggers et al. |
| 5,054,492 A | 10/1991 | Scribner et al. |
| 5,078,717 A | 1/1992 | Parins et al. |
| 5,078,723 A | 1/1992 | Dance et al. |
| 5,122,137 A | 6/1992 | Lennox |
| 5,125,928 A | 6/1992 | Parins et al. |
| 5,207,681 A | 5/1993 | Ghadjar et al. |
| 5,267,960 A | 12/1993 | Hayman et al. |
| 5,281,218 A | 1/1994 | Imran |
| 5,306,244 A | 4/1994 | Shiber |
| 5,342,357 A | 8/1994 | Nardella |
| 5,373,849 A | 12/1994 | Maroney et al. |
| 5,403,311 A | 4/1995 | Abele et al. |
| 5,429,582 A | 7/1995 | Williams |
| 5,437,662 A | 8/1995 | Nardella |
| 5,438,997 A | 8/1995 | Sieben et al. |
| 5,596,990 A | 1/1997 | Yock et al. |
| 5,599,346 A | 2/1997 | Edwards et al. |
| 5,606,974 A | 3/1997 | Castellano et al. |
| 5,636,644 A | 6/1997 | Hart et al. |

(Continued)

*Primary Examiner* — Brian Casler
*Assistant Examiner* — James Kish
(74) *Attorney, Agent, or Firm* — Vista IP Law Group LLP

(57) ABSTRACT

A medical system includes an inner core and an imager located at the distal end of the inner core, wherein the imager is extendable from within an elongated tubular member and configured to penetrate a body tissue within a living body. The elongated tubular member is configured to slideably receive the inner core. The inner core is configured to rotate radially around a longitudinal axis of the elongated member, and the imager can be configured to image a body tissue and output an image signal to an imaging system communicatively coupled with the imager. The imaging system is configured to generate an image of the body tissue from the image signal of the imager when the imager is rotated and placed into contact with the body tissue.

16 Claims, 9 Drawing Sheets

U.S. PATENT DOCUMENTS

| | | |
|---|---|---|
| 5,649,941 A | 7/1997 | Lary |
| 5,651,364 A | 7/1997 | Yock |
| 5,665,062 A | 9/1997 | Houser |
| 5,690,117 A | 11/1997 | Gilbert |
| 5,699,805 A | 12/1997 | Seward et al. |
| 5,713,363 A | 2/1998 | Seward et al. |
| 5,724,975 A | 3/1998 | Negus et al. |
| 5,724,977 A | 3/1998 | Yock et al. |
| 5,752,518 A | 5/1998 | McGee et al. |
| 5,810,764 A | 9/1998 | Eggers et al. |
| 5,829,439 A | 11/1998 | Yokosawa et al. |
| 5,830,222 A | 11/1998 | Makower |
| 5,830,224 A | 11/1998 | Cohn et al. |
| 5,904,711 A | 5/1999 | Flom et al. |
| 5,921,982 A | 7/1999 | Lesh et al. |
| 5,928,229 A | 7/1999 | Gough et al. |
| 5,980,480 A | 11/1999 | Rubenstein et al. |
| 6,080,152 A | 6/2000 | Nardella et al. |
| 6,086,534 A | 7/2000 | Kesten |
| 6,120,516 A | 9/2000 | Selmon et al. |
| 6,152,938 A | 11/2000 | Curry |
| 6,157,852 A | 12/2000 | Selmon et al. |
| 6,159,225 A | 12/2000 | Makower |
| 6,183,442 B1 * | 2/2001 | Athanasiou et al. .......... 604/154 |
| 6,245,026 B1 | 6/2001 | Campbell et al. |
| 6,277,064 B1 | 8/2001 | Yoon |
| 6,302,875 B1 | 10/2001 | Makower et al. |
| 6,319,189 B1 | 11/2001 | Halpern et al. |
| 6,371,919 B1 | 4/2002 | Tanner et al. |
| 6,375,615 B1 | 4/2002 | Flaherty et al. |
| 6,387,043 B1 | 5/2002 | Yoon |
| 6,394,956 B1 | 5/2002 | Chandrasekaran et al. |
| 6,415,823 B1 | 7/2002 | Vasek et al. |
| 6,432,104 B1 | 8/2002 | Durgin et al. |
| 6,464,693 B1 | 10/2002 | Andrews et al. |
| 6,485,465 B2 | 11/2002 | Moberg et al. |
| 6,514,248 B1 | 2/2003 | Eggers et al. |
| 6,575,928 B2 | 6/2003 | Saul et al. |
| 6,925,323 B2 | 8/2005 | Snoke |
| 7,455,666 B2 | 11/2008 | Purdy |
| 2003/0014016 A1 * | 1/2003 | Purdy .......................... 604/174 |
| 2003/0088245 A1 | 5/2003 | Woloszko et al. |

* cited by examiner

SYSTEMS AND METHODS FOR INTERNAL TISSUE PENETRATION

RELATED APPLICATION DATA

The present application is a continuation of U.S. patent application Ser. No. 10/394,079, filed Mar. 21, 2003, now U.S. Pat. No. 7,715,896, the priority of which is claimed under 35 U.S.C. §120, and the contents of which is incorporated herein by reference in its entirety, as though set forth in full.

FIELD OF INVENTION

The field of the invention relates generally to medical devices, and more particularly to a medical devices for penetrating a body tissue of a living being.

BACKGROUND

Catheters are tools commonly employed to help diagnose and treat medical conditions by allowing access to remote locations within a living body. A wide range of medical procedures can be performed with a catheter, such as imaging, angioplasty and the release of therapeutic agents into the body. Catheters provide particular advantages when used to gain access to regions of the body otherwise reachable only with invasive surgery.

Catheters are most often used in diagnosing and treating atherosclerosis and other arterial diseases with procedures such as angioplasty. In angioplasty, a balloon located on a catheter is placed within a constricted artery and inflated so as to break apart occlusive plaque and restore normal blood flow to the artery. In order to place the balloon within the constricted artery, the catheter is typically advanced through various body lumens, such as arteries and blood vessels within the circulatory system. By this nature, navigation through these lumens is generally unrestricted.

However, catheters are frequently adopted to navigate to other regions of the body, outside the circulatory system. In these cases, access can be restricted by one or more body tissues. In many cases the only way to reach the desired location is to advance the catheter through the obstructing tissue. Various systems and methodologies have been developed to penetrate the obstructing tissue. For instance, some systems rely on piercing instrumets such as a needle, located within the catheter, to pierce the tissue and create an opening through which the catheter can be advanced. Other systems rely on a drilling instrument, where an actual drill bit is used to penetrate the material. These systems are very inaccurate and can easily damage other tissues within the body.

For instance, these systems typically run the risk of "overshoot," which occurs when the various instrument advances further than intended, either too far into the body tissue or entirely through the body tissue and into a second tissue. These instruments also run the risk of damaging body tissue by mere incidental contact with another tissue. In addition, these systems are often encumbered by the penetrating instrument, which must be incorporated into the catheter along with the other medical or imaging devices already in place. Furthermore, these instruments are effectively blind when penetrating a tissue, in which case penetration can occur directly into a blood vessel or other vital organ resulting in a serious health risk to the patient.

Thus, there is a need for improved systems and methods of penetrating internal body tissues.

SUMMARY OF THE INVENTION

An improved medical device such as a catheter preferably includes an inner core and an imager that is extendable from an elongated tubular member and configured to penetrate body tissue within a living body.

Described next is an example embodiment of a method of using an improved catheter to penetrate a body tissue. First, a distal end of the elongated member is advanced into proximity with a body tissue. Then an inner core within the elongated member is rotated radially around a longitudinal axis of the member. The tissue is then imaged with an imager located at the distal end of the inner core to locate an optimum penetration region. After locating the region, the distal end of the inner core is advanced past the distal end of the elongated member such that the core is placed into contact with the tissue at the optimum region. Then, the tissue is penetrated by the rotation of the imager and creates an opening. In one embodiment, during the penetration the imager is imaging to provide a more accurate penetration of the tissue and to ensure that the inner core remains placed over region.

In another example embodiment, the improved medical device includes an elongated tubular member having a distal end and configured to slideably receive an inner core. The distal end is further configured to allow the inner core to advance outside the elongated member. The inner core has a distal end and is configured to rotate radially around a longitudinal axis of the elongated member. The device further includes an imager located at the distal end of the inner core, wherein the imager is configured to image a body tissue and output an image signal to an imaging system communicatively coupled with the imager. The imaging system is configured to generate an image of the body tissue from the image signal of the imager when the imager is rotated and placed into contact with the body tissue such that the imager penetrates the body tissue.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The details of the invention, both as to its structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DETAILED DESCRIPTION OF THE ILLUSTRATED EMBODIMENTS

The systems and methods described herein provide for the penetration of a body tissue inside a living body. In a preferred embodiment, a medical device, such as catheter, is inserted into a living body and used to penetrate the body tissue. For the sake of convenience, reference is made to the example embodiment of a catheter; however, such catheter embodiments can be adapted to be non-catheter embodiments. An inner core within the catheter is rotated and placed into direct contact with a body tissue and penetrates the tissue, creating an opening through which the catheter can be passed. Preferably, the inner core includes an imager configured to image the body tissue in order to determine an optimum location to penetrate and to image the tissue during penetration. The catheter is connected to an imaging system where the image can be displayed and used in medical diagnosis and treatment.

Figure 1:
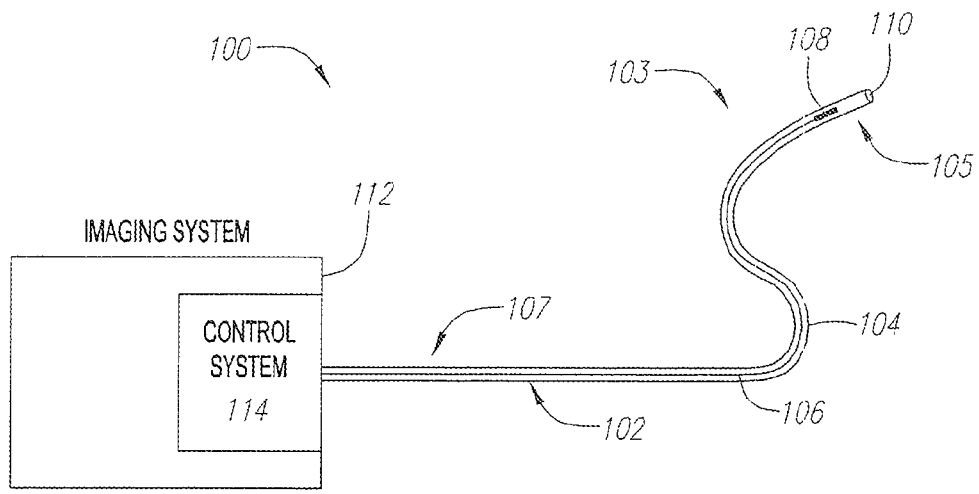
FIG. 1 is a schematic diagram depicting an example embodiment of a medical system.

FIG. 1 depicts medical system 100, which is a preferred embodiment of the systems and methods described herein. This embodiment includes medical device 102, which is preferably a catheter, elongated tubular member 104 and inner core 106, which includes imager 108. Catheter 102 is insertable into a living body and can be advanced through a body lumen such as a blood vessel, artery, or a body canal, while at the same time imaging that body lumen or canal. Catheter 102 includes distal end 103 and proximal end 107. Also depicted in medical system 100 is imaging system 112 and control system 114. Medical system 100 is configured to enable a user to image the interior of the body in order to navigate and advance catheter 102 throughout the body. This also allows catheter 102 to image the body tissue in order to locate an optimum penetration region in the tissue. What is regarded as an optimum region in the tissue is dependent on the type of tissue and application involved. For instance, an optimum region in one case may be a region devoid of blood vessels, while in another case, the region may be unobstructed on the opposite side. Imaging system 112 includes the imaging software and hardware that is used to view the interior image of the body. Control system 114 controls the rate of rotation of inner core 106 and can also be configured to control the rate of advancement of elongated member 104, inner core 106 or both.

Figure 2A:
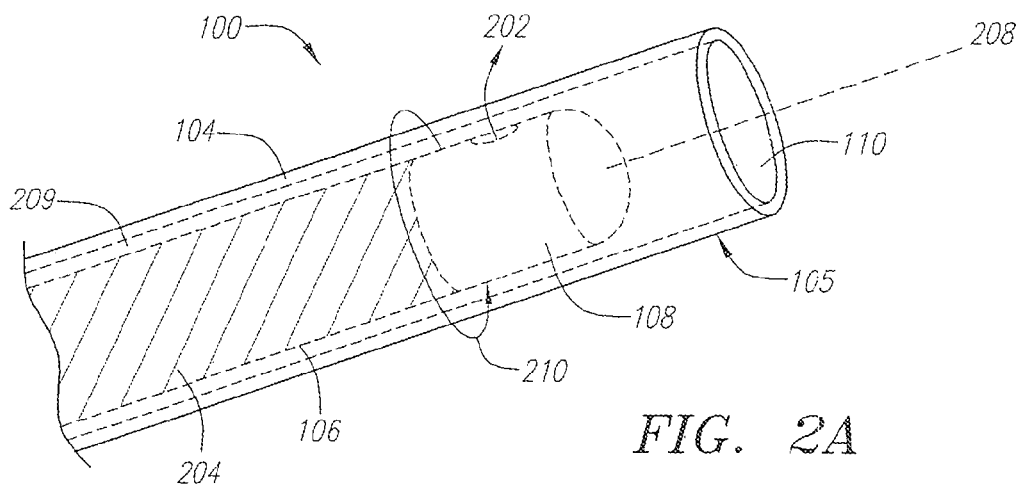
FIG. 2A is a perspective view of an example embodiment of a catheter within the medical system.

FIG. 2A depicts an example embodiment of distal end 103 of catheter 102 including elongated member 104 and inner core 106. Elongated member 104 is preferably composed of a flexible material and is shaped in a tubular manner, hollowed in the center to slideably receive inner core 106. In this embodiment, inner core 106 is configured to move axially along center longitudinal axis 208 of elongated member 104 and also to rotate radially around axis 208. Inner core 106 includes drive shaft 204 and a signal line (not shown). Opening 110 allows inner core 106 to slide outside of distal end 105 of elongated member 104. Opening 110 can be open or collapsible, depending on the needs of the application. In embodiments where the distance between inner core 106 and elongated member 104 is small, catheter fluid 209 does not substantially flow out of opening 110 due to the cohesive forces acting upon fluid 209. Control system 114 can include a check valve to add more fluid 209 if needed. A collapsible opening 110 may be desired in applications where the escape of catheter fluid 209 or entry of body fluids into catheter 102 is undesirable.

Imager 108 is preferably located at the distal end of inner core 106 so that when inner core 106 is advanced outside of elongated member 104, imager 108 is placed into contact with a body tissue. When inner core 106 is rotating and in contact with the body tissue, imager 108 bores or penetrates into the body tissue. If contact with the body tissue is maintained, the continual penetration of the body tissue by imager 108 will create an opening in the tissue through which catheter 102 can pass. Catheter 102 can then be advanced to a desired region within the living body.

Imager 108 may be any kind of known imager that is capable of imaging in a rotational manner and may be, for example, a forward-facing or side-facing acoustic transducer or a light-based optical imager such as one based on optical coherence tomography (OCT) or optical coherence domain reflectometry (OCDR). For ease of discussion, imager 108 will be described herein as an acoustic transducer configured to image uni-directionally, or from one direction, indicated by directional arrow 202. In other embodiments, imager 108 can be adapted to image in a multi-directional or omni-directional configuration. Acoustic transducer 108 operates in a typical manner by first sending an acoustic pulse outward in direction 202 and then receiving a reflection of that pulse. Once the reflected pulse is received, transducer 108 generates an image signal and outputs the signal to imaging system 112 by way of the signal line. These steps make up one transducing cycle and preferably there are multiple cycles for every rotation of inner core 106.

All communication between transducer 108 and imaging system 112 occurs by the signal line, which is preferably located at the center of inner core 106 within drive shaft 204. The send and receive process occurs while transducer 108 is rotating and numerous signals can be sent and received in the span of one rotation. Imaging system 112 can then assemble an image of the surrounding body tissue with the information provided by these image signals. The image can be configured to display any combination of anatomical, morphological, topological or temperature information of the surrounding tissue.

Control system 114 operates to rotate drive shaft 204 and transducer 108 radially around axis 208. This radial motion is depicted by directional arrow 210. Control system 114 tracks the radial position of transducer 108, including the orientation of receiving direction 202, which allows each received reflected signal to be correlated with the corresponding position on the body tissue. In addition, control system 114 can be configured to move inner core 106 axially along center longitudinal axis 208. Control system 114 again tracks the position of transducer 108 and correlates each image signal to the axial position of transducer 108.

Of course, as with all embodiments described in this specification, a sonolucent window (not shown) and other features known to those of skill in the art of medical imaging and/or catheter design, including for example guidewires, guiding catheters, inflatable balloons, drug delivery systems and heat-applying devices, may be included. Although the applications and implementations of catheter 102 may vary, in a typical embodiment elongated member 104 is filled with catheter fluid 209, such as saline, and inserted into a lumen of a body, such as a blood vessel, coronary artery or spinal canal.

Figure 2B:
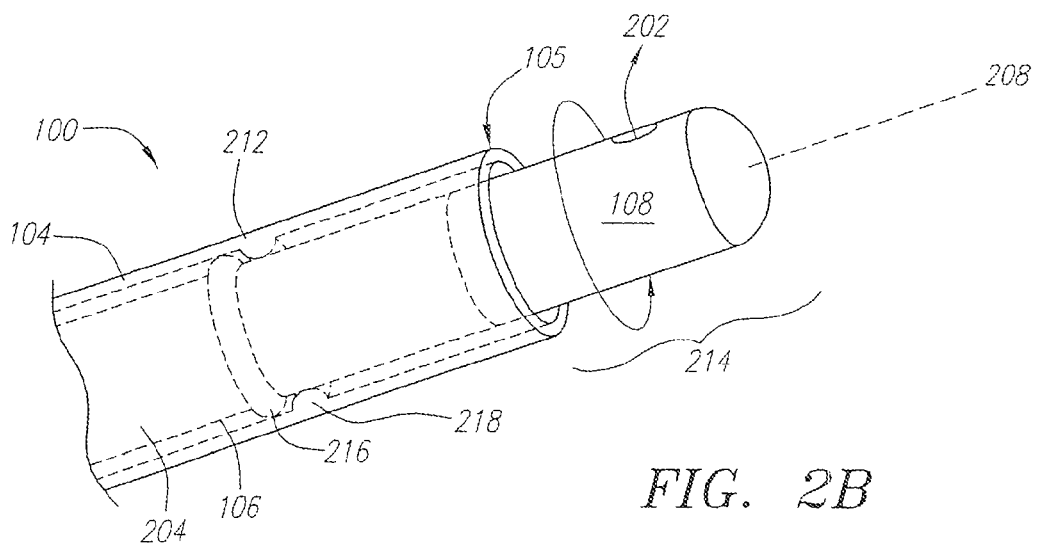
FIG. 2B is a perspective view of another example embodiment of a catheter within the medical system.

FIG. 2A depicts inner core 106 in a retracted state within elongated member 104. FIG. 2B depicts inner core 106 in an extended state after it has been advanced past distal end 105 and outside of elongated member 104. Once inner core 106 is extended past distal end 105 it can be placed in physical contact with a body tissue and used to penetrate the tissue. In one embodiment, system 100 includes stop device 212, which stops the advancement of inner core 106 once pre-determined length 214 of inner core 106 has advanced past distal end 105. Stop device 212 can be any device which limits the advancement of inner core 106. In this embodiment, stop device 212 includes detent 216 in inner core 106 and detent 218 on the interior surface of elongated member 104. Detents 216 and 218 are preferably positioned so that they come into contact and stop the advancement of inner core 106 once pre-determined length 214 has been reached. Pre-determined length 214 can be any length suitable for the needs of the application. In one embodiment, length 214 is the slightly less than the length of transducer 108 in order to prevent exposure of the abrasive surface of drive shaft 204 to any surrounding body tissue.

FIG. 2B depicts an embodiment of stop device 212 located at distal end 103 of catheter 102. Of course, one of skill in the art will readily envision other embodiments similar in effect, including positioning stop device 212 at proximal end 107 of catheter 102. In addition, many alternative embodiments of the structure of stop device 212 can be implemented, including preventing the advancement of inner core 106 automatically through the use of software and/or hardware within control system 114. In one embodiment, control system 114 includes a gauging device configured to gauge the distance inner core 106 has advanced. This gauging device can be implemented automatically with the use of hardware or software within control system 114, or it can be implemented manually, for instance through the addition of a gauge or index at the proximal end of catheter 102, in view of the user operating system 100.

Figure 3A:
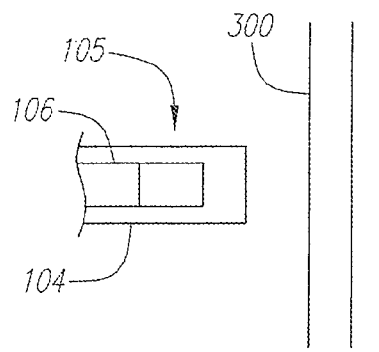
FIGS. 3A-G are perspective views of additional example embodiments of a catheter within the medical system.
Figure 3B:
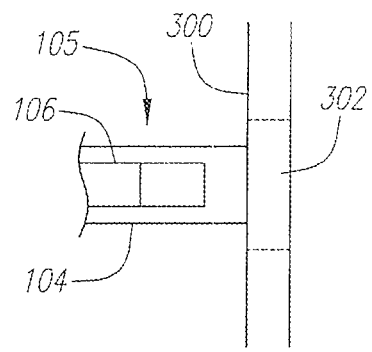
Figure 3C:
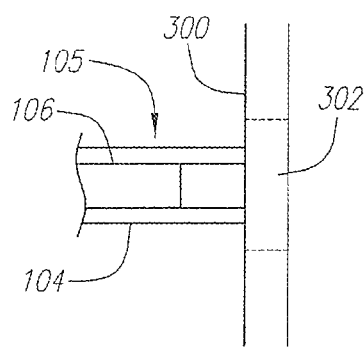

FIGS. 3A-G depict one embodiment of system 100 at various stages in the tissue penetration process. FIG. 3A depicts an embodiment of catheter 102 in proximity with body tissue 300 that requires penetration. FIG. 3B depicts distal end 105 in physical contact with body tissue 300 at optimum penetration region 302. In one embodiment, transducer 108 images body tissue 300 to aid in locating optimum penetration region 302. Whether imaging of body tissue 300 is performed is dependent on the individual application and medical procedure. FIG. 3C depicts inner core 106 in direct physical contact with tissue 300 at optimum penetration region 302. If imaging is performed, then inner core 106 is rotating prior to contacting tissue 300. However, in an embodiment where no imaging is performed, control system 114 can initiate rotation of inner core 106 either before or after contacting inner core 106 with tissue 300.

Figure 3D:
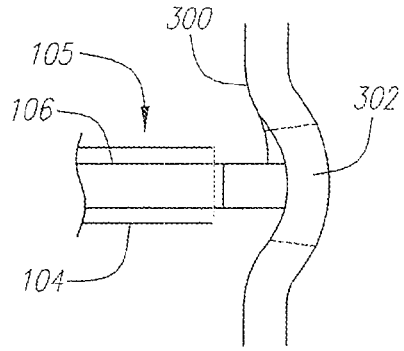

FIG. 3D depicts inner core 106 in an extended state advanced from within elongated member 104 and inner core 106 has penetrated a portion of tissue 300. Some deflection of tissue 300 has occurred due to the advancement of inner core 106 prior to total penetration of tissue 300. The amount of deflection that occurs is dependent on the thickness and rigidity of tissue 300, as well as the rate of penetration of inner core 106, which will be discussed in more detail below. In some embodiments, for instance in the implantation of a radioactive substance in a tumor, only partial penetration is desired and once that amount of penetration is reached, inner core 106 can then be retracted or rotation of inner core 106 can be stopped.

Figure 3E:
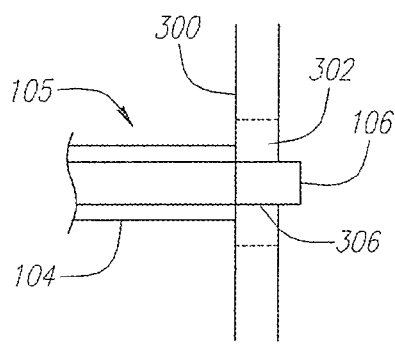
Figure 3F:
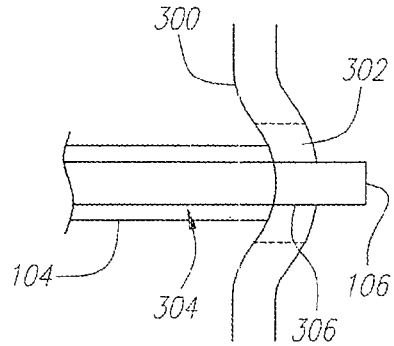
Figure 3G:
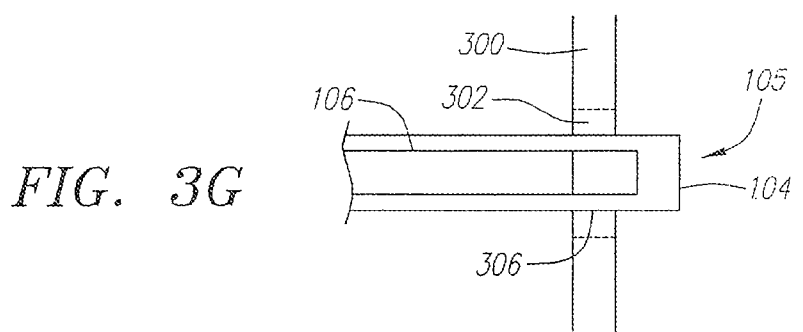

FIG. 3E depicts an embodiment where total penetration of tissue 300 is desired and accordingly inner core 106 is shown after it has penetrated tissue 300 and created opening 306 in region 302. FIG. 3F depicts an embodiment where catheter 102 is in the process of advancing through tissue 300. In this embodiment axial pressure is applied to elongated member 104 while inner core 106 is extended and the resulting force on tissue 300 causes some deflection of tissue 300 as depicted. Again, the amount of deflection of tissue 300 depends in part on the thickness, rigidity and type of tissue 300 being penetrated. The amount of deflection also depends on the distance 304 between inner core 106 and the outer surface of elongated member 104, where the smaller distance 304 requires a smaller amount of axial pressure to force catheter 102 through opening 306 and accordingly results in a smaller amount of deflection of tissue 300. Therefore, for sensitive applications and procedures requiring a low amount of deflection, distance 304 is preferably kept to a minimum. It will be readily apparent to one of skill in the art the numerous ways in which distance 304 can be adjusted, including changing the distance between the outer surface of inner core 106 and the inner surface of elongated member 104 as well as using a thinner material for elongated member 104. FIG. 3G depicts distal end 105 of elongated member 104 after it has been advanced through opening 306 in tissue 300.

Figure 4:
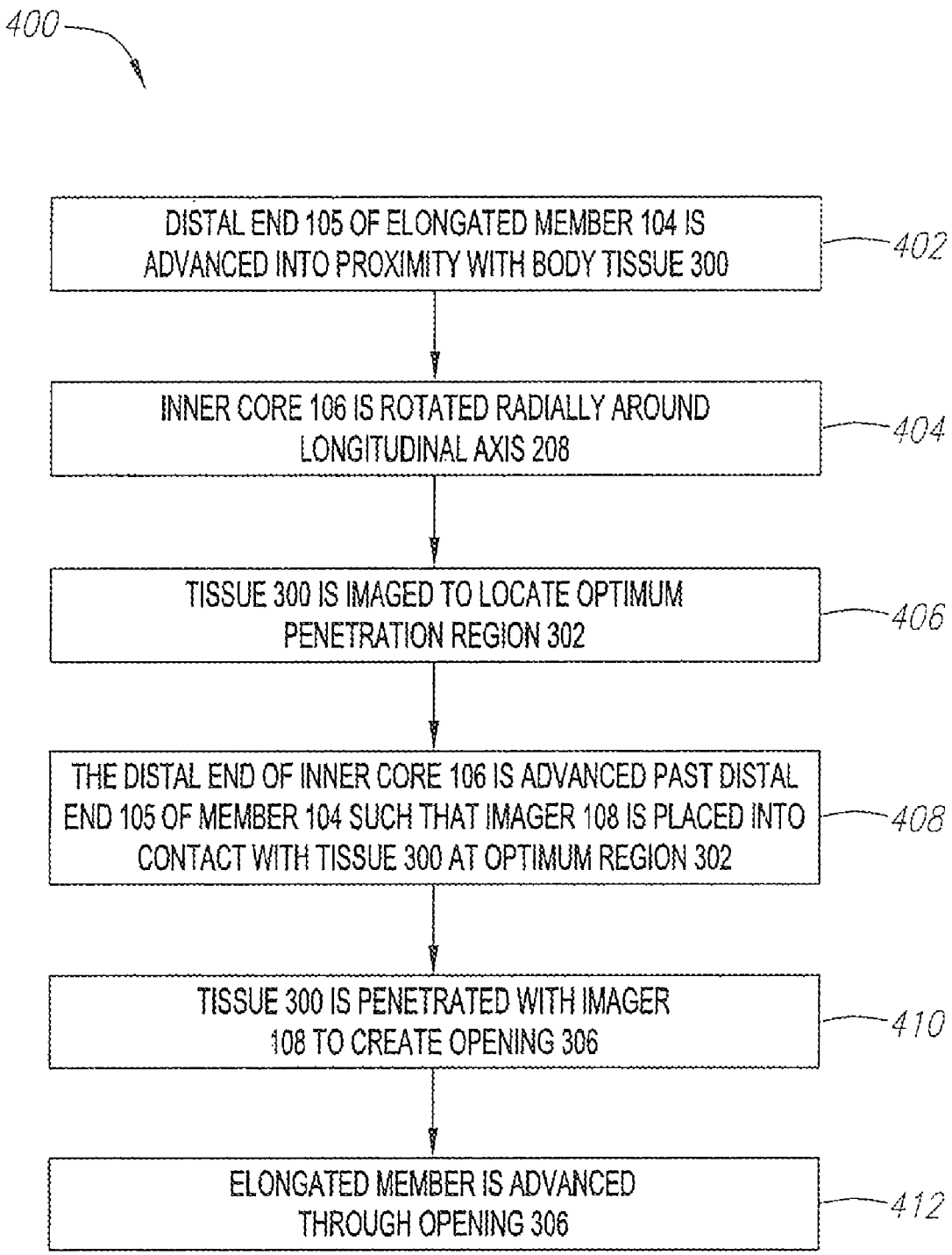
FIG. 4 is a flow diagram of an example embodiment of penetration process.

FIG. 4 depicts one embodiment of an example penetration process 400 performed within a living body. At 402, distal end 105 of elongated member 104 is advanced into proximity with body tissue 300. Next, at 404, inner core 106 is rotated radially around longitudinal axis 208 and at 406, tissue 300 is imaged to locate optimum penetration region 302. At 408, the distal end of inner core 106 is advanced past distal end 105 of member 104 such that imager 108 is placed into contact with tissue 300 at optimum region 302. It should be noted that the rotation of inner core 106 can be initiated after it has already been advanced from within member 104, however, this sacrifices any imaging capability until inner core 106 begins rotating. Then, at 410, tissue 300 is penetrated with imager 108 to create opening 306. During the penetration, imager 108 is preferably imaging to provide a more accurate penetration of tissue 300 and to ensure that inner core 106 remains placed over region 302. Finally, at 412, elongated member is advanced through opening 306.

The rate of penetration of tissue 300 is dependent on the type of body tissue 300 as well as the rate of rotation of inner core 106, the shape and configuration of transducer 108 and the axial force applied to advance inner core 106. In many embodiments, a low rate of penetration is desired in order to increase the accuracy and precision in penetration as well as to reduce the risk of overshoot. However, a low rate of penetration can still require a high amount of axial force or an abrasive configuration if the body tissue 300 is very hard or resilient to penetration.

Figure 5A:
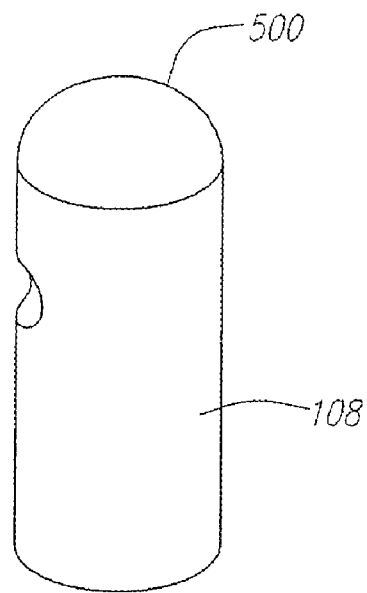
FIGS. 5A-I are perspective views of example embodiments of a transducer within the medical system.
Figure 5B:
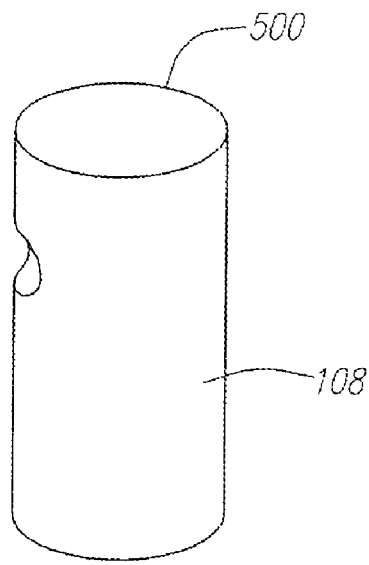

System 100 can be configured to penetrate all types of body tissue 300 and transducer 108 can be independently configured to facilitate penetration of each type of body tissue 300. To achieve the same rate of penetration, softer tissues generally require less abrasive configurations than harder tissues. For instance, in embodiments requiring penetration of soft tissue such as skin or membranes, transducer 108 can assume a typical transducer shape where distal end 500 is rounded, such as in the embodiment depicted in FIG. 5A. Alternatively, in the embodiment depicted in FIG. 5B, distal end 500 of transducer 108 can be substantially flat. Both of these embodiments reduce the risk that transducer 108 will inadvertently penetrate the interior of elongated member 104. Penetration of elongated member 104 is not desirable because it can damage surrounding tissue, result in loss of catheter fluid 109 and even separation of elongated member 104, in which case surgery may be required to remove the severed portion.

Figure 5C:
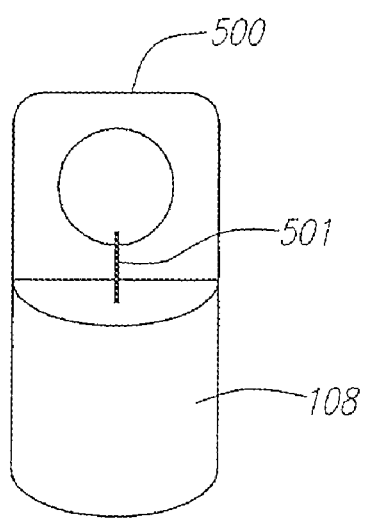
Figure 5D:
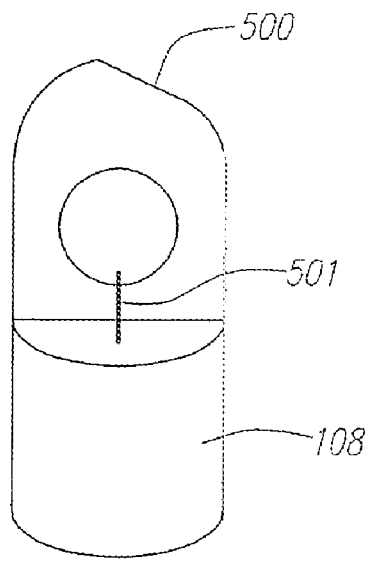

FIGS. 5C-D depict other embodiments of transducer 108. These embodiments depict transducer 108 in a related structural configuration, including electrical connection 501. In the preferred embodiment depicted in FIG. 5C, distal end 500 of transducer 108 is rounded with a substantially flat surface, while in the embodiment depicted in FIG. 5D, the flat surface located at distal end 500 is offset at an angle to facilitate penetration of body tissue 300.

Figure 5E:
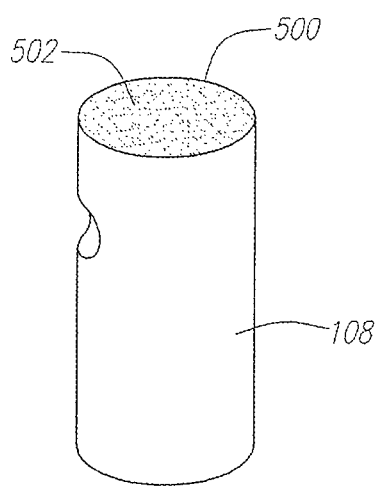
Figure 5F:
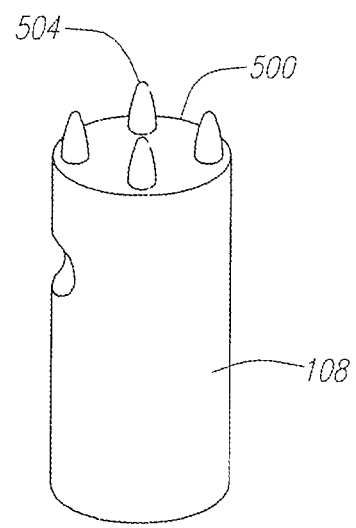

In instances where harder or more resilient tissues 300 are penetrated, distal end 500 of transducer 108 can be configured accordingly. FIGS. 5E-I depict various embodiments of transducer 108 configured to penetrate a harder tissue 300 or to penetrate tissue at a faster rate. FIG. 5E depicts an embodiment where distal end 500 includes an abrasive surface 502 and a pointed tip. Abrasive surface 502 can be attached in any manner or it can be formed on distal end 500 directly. FIG. 5F depicts a similar embodiment where distal end 500 includes protrusions 504. Again, protrusions 504 can be formed directly on transducer 108 or can be separately attached. The shape and configuration of protrusions 504 is dependent on and may vary with the individual application.

Figure 5G:
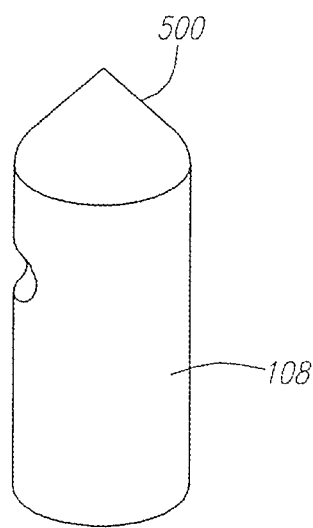
Figure 5H:
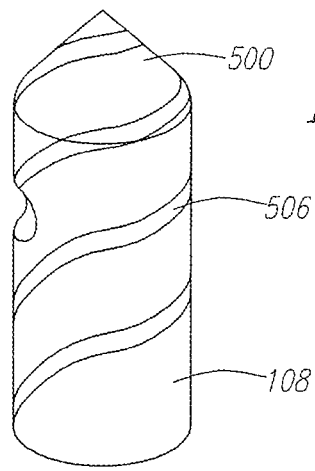
Figure 5I:
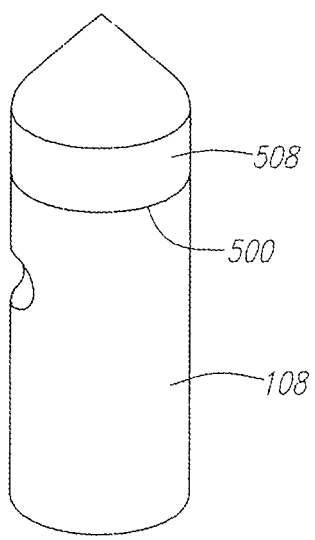

FIGS. 5G-I depict embodiments of transducer 108 where distal end 500 is pointed to facilitate penetration. In FIG. 5G, distal end 500 is pointed but the surface of transducer 108 is relatively smooth. In FIG. 5H, distal end 500 is also pointed but the surface of transducer 108 includes flute 506, which is configured to cut tissue 300. This and similar embodiments can be used in procedures where a very hard tissue 300, such as bone or plaque, is penetrated. FIG. 5I depicts an embodiment where distal end 500 is coupled with a drill member 508. In each of the embodiments depicted, transducer 108 is configured to both facilitate penetration and at the same time allow imaging to take place without significant obstruction. In other embodiments where imager 108 utilizes an alternative type of imaging, a similar allowance between penetration and imaging capability is also envisioned. Furthermore, one of skill in the art will recognize that various configurations of end 500 will affect the risk of snagging or catching tissue 300 during penetration, which could result in inadvertent severance of inner core 106. One of skill in the art will balance the nature and type of tissue 300 with the risks of inadvertent penetration of member 104 and inadvertent damage to inner core 106 and the surrounding tissue when determining the embodiment of transducer 108 that is most suitable for the application.

In addition to the configuration of transducer 108, the rate of penetration is dependent on the rate of rotation of inner core 106 as well as the axial force applied to inner core 106. A high rate of rotation of inner core will result in a higher rate of penetration. System 100 can operate with any rate of rotation. However, because the rotation rate can directly effect the imaging capability, system 100 is preferably designed to achieve the desired rate of penetration while remaining within a rotation rate suitable for imaging. For instance, in one embodiment, inner core 106 rotates at a rate at approximately 840-1800 revolutions per minute and there are approximately 256 transducing cycles per rotation. In this embodiment, the rate of rotation is independent of the number of transducing cycles in each rotation. The rate of penetration is also dependent on the axial force applied to inner core 106, where a higher axial force pushing inner core 106 distally towards tissue 300 results in a higher rate of penetration. However, a higher axial force places stress on catheter 102 and could force catheter to bend and rupture surrounding body tissues. Also, a higher axial force could result cause inner core 106 to overshoot and damage surrounding tissue. Thus, an appropriate amount of axial force should be used for each particular application.

As inner core 106 rotates, a level of torque is generated upon inner core 106. This torque level is dependent on the inertia of core 106 as well as the friction between core 106 and the surroundings, such as fluid 209 and member 104. When the level of torque becomes high enough, inner core 106 can buckle or break. When this occurs, inner core 106 has reached a maximum torque threshold. This level of torque can increase significantly while inner core 106 is penetrating tissue 300. In any of the embodiments, control system 114 may be configured to measure the level of torque applied to inner core 106. Control system 114 can then reduce the rate of rotation of inner core 106 or stop the rotation altogether if the maximum torque threshold is reached in order to prevent buckling, breakage, severance or any other undesirable torque-induced effects. Furthermore, control system 114 can output the torque measurement to imaging system 112 where it can be displayed and monitored by a user.

Also, the level of torque can be correlated to the point where inner core 106 comes into contact with body tissue 300 and penetrates tissue 300. The added friction caused by the penetration process increases the level of torque applied to inner core 106. By measuring the torque level, system 100 can indicate when penetration of tissue 300 has begun and when inner core 106 has penetrated tissue 300 entirely. In one embodiment, a pre-determined level of torque indicates when core 106 has penetrated all of tissue 300 and control system 114 is configured to stop rotation once this pre-determined level is reached. This reduces the risk of overshoot. The pre-determined level will vary dependent upon the application and the nature of tissue 300. In one embodiment, a baseline torque level is determined when system 100 is rotating but not penetrating tissue and the predetermined level is set to this baseline value. As core 106 penetrates the tissue, the torque level rises and when the penetration is complete, the torque level decreases to a value at or near the pre-determined value. Control system 114, configured to measure the torque level, recognizes this decrease and terminates the rotation to prevent damage to any surrounding tissues. In addition, the pre-determined level can be set at or just below the torque threshold to prevent damage to core 106.

Figure 6:
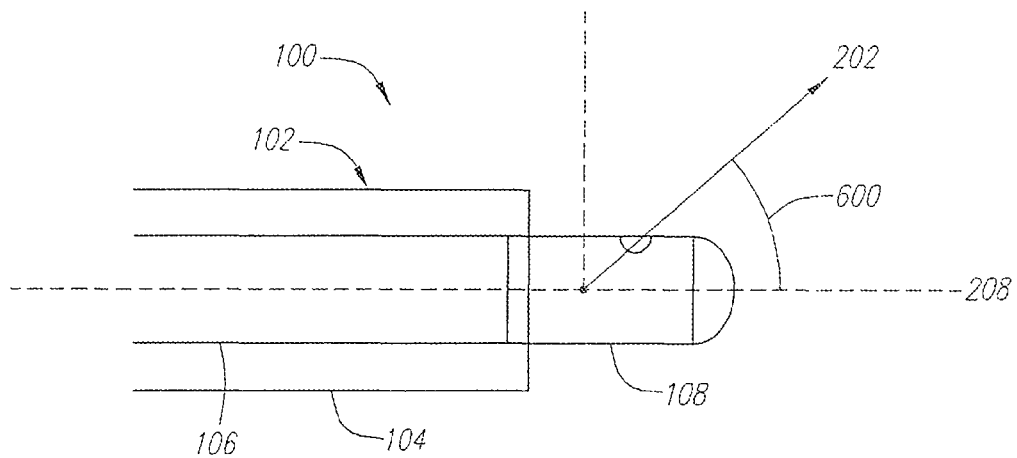
FIG. 6 is a perspective view of another example embodiment of a catheter within the medical system.

FIG. 6 depicts one embodiment of system 100, including inner core 106 in an extended state. Direction 202 is measured by offset angle 600, which is the angular offset of direction 202 from longitudinal center axis 208. As stated above, direction 202 is the direction in which transducer 108 sends and receives acoustic or other imaging signals. Accordingly, direction 202 determines where transducer 108 can image. When offset angle 600 is 90 degrees, direction 202 is perpendicular with axis 208 and transducer 108 is in a side facing configuration and can image body tissue located along the sides of transducer 108. When offset angle 600 is, decreased, transducer 108 is capable of imaging body tissue located distally to transducer 108 and is in a forward-facing configuration. As offset angle 600 decreases, transducer 108 is capable of imaging body tissue located further distally to transducer 108. This may be desirable when the user wants system 100 to image body tissue 300 located distal to transducer 108 in order to locate optimum penetration region 302.

However, if offset angle 600 is too low, for instance if offset angle 600 were 0 degrees, system 100 may not create a desired body tissue image. This is because imaging system 112 requires transducer 108 to image multiple different locations in every rotation and an offset angle of 0 degrees would allow transducer 108 to image only one location directly distal to transducer 108 along axis 208. The minimum offset angle 600 varies accordingly with the imaging capabilities of system 100. Generally, a lower offset angle will allow tissue located more distally to transducer 108 to be imaged, however the image is typically reduced in quality because image interpretation becomes more difficult. Therefore, the offset angle 600 used may be varied based on the needs of each individual application. If only imaging of the tissue surrounding transducer 108 is desired, then direction 202 can be perpendicular to axis 208. For instance, this might be the case if system 100 were implemented in an angioplasty procedure and catheter 102 was inserted into a body lumen requiring imaging capability of tissue directly surrounding transducer 108. Conversely, if forward imaging capabilities are needed, then direction 202 can be any angle less than 90 degrees and preferably greater than the minimum offset angle. In one embodiment, angle 600 is approximately 0-45 degrees, and in a preferred forward-looking embodiment, angle 600 is 45 degrees. However, one of skill in the art will readily recognize any offset angle can be used depending on the needs of the application.

Figure 7A:
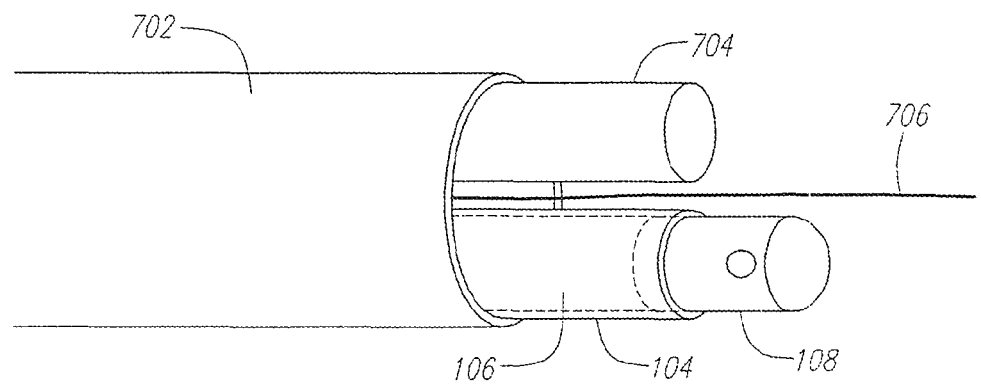
FIGS. 7A-B are perspective views of additional example embodiments of a catheter within the medical system.

In any of the embodiments, the system may include a suction system configured to suction, or apply negative pressure, within the body. The suction system allows the removal of excess fluid and debris from within the body. For instance, the suction system can remove debris resulting from tissue penetration or blood or other excess bodily fluids. The suction system can be a vacuum or pump system coupled with proximal end 107 of catheter 102. In this embodiment, there is preferably enough space between elongated member 104 and inner core 106 to allow the flow of the fluid and any debris within the fluid proximally through member 104 and into a reservoir or disposal system. FIG. 7A depicts another embodiment of medical system 100 where the suction system (not shown) is coupled with elongated tubular suction member 704. Both elongated member 104 and elongated suction member 704 are slideably received by elongated tubular guide member 702.

The suction system can also be configured to apply negative pressure to body tissue 300 and fixate the tissue with respect to inner core 106. This can facilitate penetration process 400 by decreasing the likelihood that inner core 106 will penetrate a region other than optimum penetration region 302. For instance, in this embodiment, once optimum region 302 is located the distal end of suction member 704 is placed into proximity with tissue 300 and negative pressure is applied such that the suction system fixates tissue 300. Inner core 106 is held in place with respect to suction member 704 by guide member 702 so that no inadvertent movement out of region 302 can occur. Tissue 300 can also be fixated to stabilize inner core 106 and facilitate imaging of body tissue 300. In addition to suction, fixation can be achieved by the use of other grasping devices such as hooks or very small scale forceps.

Figure 7B:
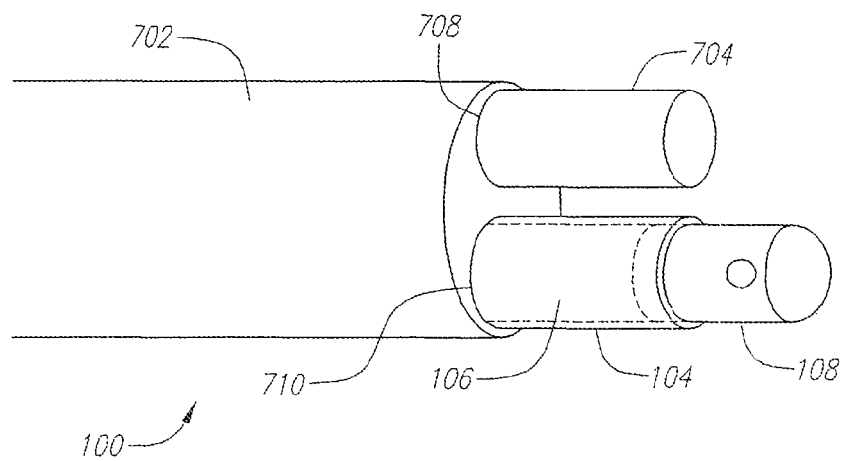

FIG. 7B depicts another embodiment of system 100 where guide member 702 includes lumens 708 and 710, each configured to slideably receive suction member 704 and elongated member 104, respectively. Guide member 702 can be configured with additional lumens to accommodate other devices insertable within the body. Also, members 104 or 704 can be withdrawn to allow insertion of an additional device into lumen 708 or 710. Accordingly, the circumference of guide member 702, as depicted in FIG. 7A, can be increased or decreased to accommodate other devices as needed by the individual application. In certain embodiments, space within the body is limited and may prevent the use of guide member 702. If suction is required in these embodiments, in can be applied directly through member 104. Also, the device within each lumen can be withdrawn and replaced by another device in order to allow the use of additional devices without adding additional circumference or lumens to guide member 702.

One of skill in the art will readily recognize the many additional devices that can be inserted within guide member 702. One example of such a device is a coagulation device configured to suppress bleeding. Several examples of coagulation devices include cryo-elements, radio frequency (RF) energy sources, diathermy devices and lasers. Coagulation devices apply energy to body tissue to suppress bleeding by that tissue, i.e., to coagulate blood in the tissue. The type of energy applied depends on the application or the type of coagulation device used, however several examples include thermal, such as with cautery or cryotherapy, RF, mechanical, electrical, acoustical or optical energy. A coagulation device can be coupled with and applied by elongated member 104, suction member 704 or an additional elongated member.

In one embodiment, imager 108 is coupled with an RF source and functions as a coagulation device by applying RF energy to the surrounding tissue as it rotates. A slip ring or commutator electrically connects the RF power supply to the outside of inner core 106, which is then connected to imager 108. This embodiment provides allows a user to coagulate and penetrate simultaneously. In another embodiment, by reducing the frequency and increasing the amplitude of the RF power supply, inner core 106 can be configured to function as an ablation device.

In the embodiment depicted in FIG. 7A, wire 706 is a coagulation device such as a single harmonic wire. Single harmonic wire 706 physically oscillates in response to acoustic energy applied by a source typically located at the proximal end of harmonic wire 706. Harmonic wire 706 can be used to physically penetrate tissue 300 prior to penetration by inner core 106. This technique facilitates the alignment of inner core 106 in the proper position in optimum region 302, both by creating a visible target for penetration by inner core 106 and by creating a path for core 106 to follow in the penetration process. In addition, harmonic wire 706 can be used as a guidewire within the body, in addition to the penetration and coagulation functions.

Figure 8A:
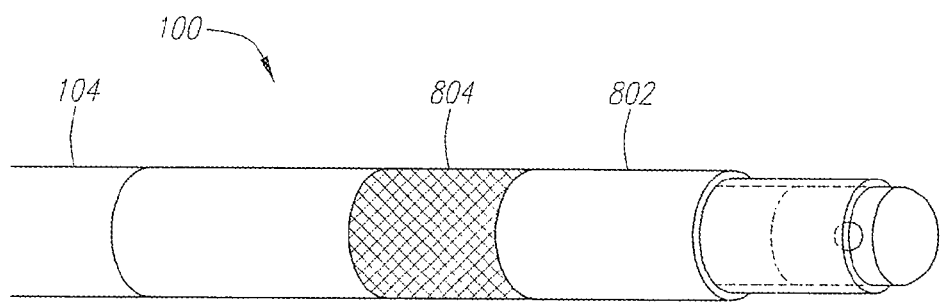
FIGS. 8A-B are perspective views of additional example embodiments of a catheter within the medical system.
Figure 8B:
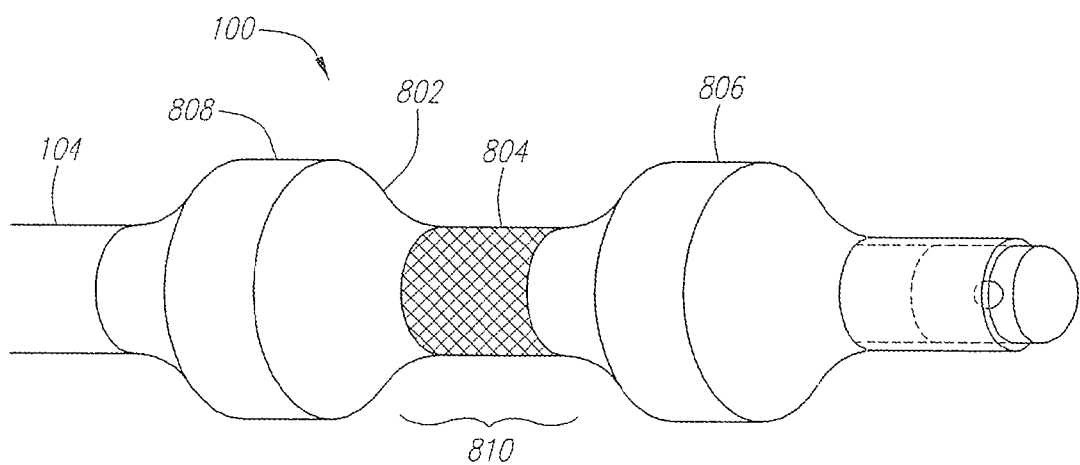

Additional devices that can be used in any of the systems include medical prostheses such as balloons, stents and shunts. FIGS. 8A-B depict and embodiment of system 100 where elongated member 104 includes multiple prostheses 802 and 804. In this embodiment prostheses 802 and 804 are a narrow dumbbell circumference balloon and an expandable stent, respectively. FIG. 8A depicts balloon 802 in an uninflated state, with stent 804 unexpanded. This embodiment is configured for use with an application of system 100 directed towards the creation of an opening in tissue 300, such as the embodiment depicted in FIGS. 3A-G. This embodiment also provides the capability to enlarge and maintain an opening once created. It should be noted that the additional inflation lumen typically necessary to inflate balloon 802 is not shown to provide ease of discussion.

The narrow dumbbell circumference configuration of balloon 802 allows easier alignment and enlargement within the opening. The ends of balloon 802, proximal end 806 and distal end 808, can be configured to inflate in sequence or simultaneously, to ensure proper alignment within the opening. For instance, in a proximal-distal inflation, member 104 is inserted within the opening and proximal end 806 is inflated on the proximal side of tissue 300. Pressure applied to member 104 in a distal direction keeps proximal end 806 in contact with tissue 300. Distal end 808 is then inflated on the distal side of tissue 300 and balloon 802 is aligned and maintained within the opening. The narrow circumference of the center portion 810 determines the extent by which the opening is enlarged or dilated. FIG. 8B depicts balloon 802 in a fully inflated state. In other embodiments, balloon 802 can be inflated in a distal-proximal manner where distal end 808 is inflated prior to proximal end 806.

Stent 804 expands as balloon 802 inflates and locks into an expanded position aligned directly with the opening. Balloon 802 is then deflated and member 104 is removed leaving stent 804 expanded within the opening and in position to maintain the opening. In other embodiments, balloon 802 and stent 804 can be used separately. One example of this is a self-expanding stent, the use of which is readily recognized by one of skill in the art. One of skill in the art will also recognize the numerous varieties of prostheses 802 and 804, and also the existence of additional types of prostheses, all of which can be included on member 104 or an addition elongated member and used in conjunction with system 100.

To further illustrate the systems and methods described herein, the implementation of medical system 100 will be discussed in an example medical environment and procedure. This example procedure involves the treatment of hydrocephalus with catheter 102. Hydrocephalus is a swelling of the interior cerebral ventricles caused by excess cerebro-spinal fluid (CSF). One type of hydrocephalus is non-communicating, or obstructive hydrocephalus, where the flow of CSF is blocked along one or more of the narrow pathways connecting the ventricles. To treat this and other types of hydrocephalus, a communicating passageway is created to allow the excess CSF to drain from the swollen ventricles. The example procedure described herein includes utilizing a percutaneous intraspinal navigation (PIN) technique to place catheter 102 into proximity with a swollen third cerebral ventricle. Catheter 102 is then used to penetrate the tissue of the third ventricle and create an opening or communicating passageway through which the excess CSF can drain. This technique offers numerous benefits over conventional techniques such as an endoscopic third ventriculostomy.

Figure 9:
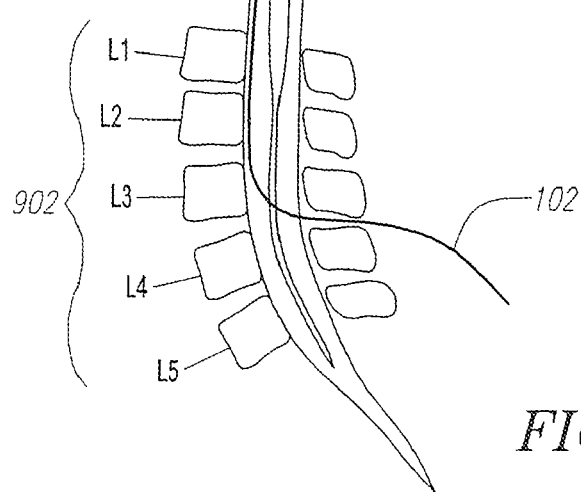
FIG. 9 is a perspective view of a central nervous system in which an example embodiment of the medical system can be implemented.

FIG. 9 depicts various portions of central nervous system 920 of living body 900 in which one embodiment of system 100 can be utilized. More specifically, FIG. 9 depicts lumbar region 902, dural membrane 904, brain 906, spinal canal 908, spinal cord 910, cranium 912, third ventricle 914, third ventricle membrane 916, CSF 918 and cistern 919. Shown within lumbar region 902 are lumbar vertebrae L1, L2, L3, L4 and L5. In this embodiment, system 100 is configured to enable the percutaneous intraspinal navigation of catheter 102 from lumbar region 902 through spinal canal 908 and into proximity with third ventricle 914. Catheter 102 preferably includes imager 108 and imaging system 112, which enables system 100 to image the interior regions of body 900, which facilitates the navigation of those regions. As mentioned above, imager 108 can use any imaging technique such as acoustic or optical imaging. For ease of discussion, imager 108 will be described as an acoustic transducer in this example environment.

Percutaneous intraspinal navigation is discussed in detail in the currently pending U.S. patent application entitled, "Methods and Apparatuses for Navigating the Subarachnoid Space," having Ser. No. 09/905,670 and filed on Jul. 13, 2001, which is hereby incorporated for all purposes herein. In one embodiment of PIN, distal end 103 of catheter 102 is inserted into spinal canal 708, also referred to as the spinal subarachnoid space, through lumbar region 902 and dural membrane 904. The insertion through region 902 is preferably in the L3-L4 or L4-L5 spaces, although any insertion location can be used.

Once within spinal canal 908, catheter 102 is navigated anteriorly through spinal canal 908 with care to avoid damage to spinal cord 910, as well as other spinal and cranial nerves. Navigation through spinal canal 908 is preferably done with the aid of acoustic imaging, however, other imaging techniques can be substituted. Catheter 102 is then navigated into cranium 912 and into proximity with third ventricle 914. Due to the narrow regions encountered in navigating through spinal canal 908, the width of elongated member 104 is kept small, preferably less than 2 mm (millimeter) or 6F (french). In one experimental embodiment, catheter 102 was a 3F catheter and incurred no noticeable damage to spinal cord 910 when navigating spinal canal 908.

Figure 10:
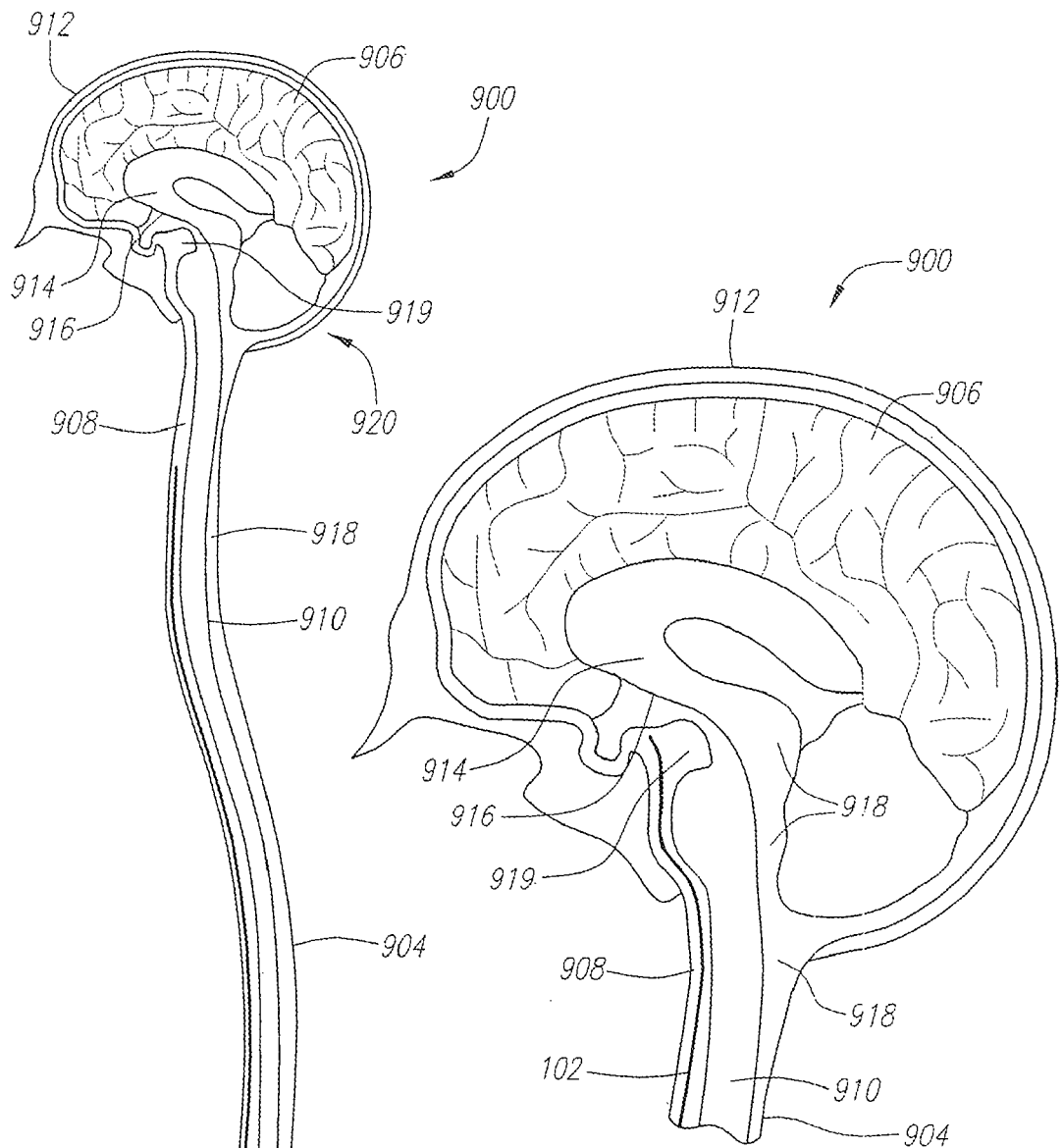
FIG. 10 a perspective view of a central nervous system in which an example embodiment of the medical system can be implemented.

FIG. 10 depicts a closer view of an embodiment of catheter 102 in proximity with third ventricle 914. Once in proximity, catheter 102 can image third ventricle membrane 916 in order to locate an optimum penetration region in membrane 916, such as region 302 in FIGS. 3B-3G. In this embodiment, the optimum penetration region 302 is preferably an area of membrane 916 that does not contain blood vessels or arteries that could pose a significant risk of bleeding. Also, the presence of achrinoid membranes can obstruct the penetration of membrane 916 by inner core 106 and the optimum penetration region 302 is preferably chosen to avoid achrinoid membranes. Once the region 302 is located, catheter 102 can then be used to penetrate third ventricle membrane 916 to allow excess CSF 918 to drain into cistern 919 and spinal canal 908. Excess CSF 918 is then absorbed and processed by body 900 and the swollen ventricles return to normal size.

Because membrane 916 is relatively soft, transducer 108 does not require extensive abrasive configurations to penetrate membrane 916. Furthermore, penetration is facilitated because membrane 916 is under pressure and stretched due to the excess CSF 918. Therefore, in a preferred embodiment, transducer 108 is configured similar to the embodiment depicted in FIG. 5B, where distal end 500 is substantially flat. This configuration can reduce the risk of damage to any tissue surrounding the penetration region. However, any configuration depicted in FIGS. 5A-G can be used to penetrate membrane 916.

To penetrate membrane 916, elongated member 104 is advanced into contact with the optimum penetration region 302 and once in place, rotating inner core 106 is also advanced into contact with the region 302 and penetrates membrane 916. Again, care is taken to avoid extending inner core 106 further than is needed to create opening 306. Preferably, stop device 212 prevents advancement of inner core 106 once pre-determined length 214 is reached. Opening 306 should be sufficiently large to allow drainage of CSF 918 without closing prematurely. The size of opening 306 is dictated initially by the diameter of transducer 108. If this size is sufficient for the needs of the procedure, then inner core 106 can be retracted within elongated member 104 and catheter 102 can be withdrawn altogether. If opening 306 needs to be enlarged, elongated member 104 can be advanced through opening 306.

Alternatively, a prosthesis, such as balloon 802 depicted in FIGS. 8A-B, can be advanced into opening 306 and inflated to enlarge opening 306. In addition, in order to maintain opening 306 and guard against premature closure, a shunt can be placed in opening 306 to allow excess CSF 918 to drain continually. In one embodiment, system 100 is configured to suction excess CSF 918 from third ventricle 914. The use of suction to remove excess CSF 918 can be used when body 900 is not uptaking or processing CSF 918 normally, for instance in the case of communicating hydrocephalus.

As in most medical processes, bleeding poses a significant risk. This risk is magnified in the present example due to the proximity of system 100 to brain 906 and spinal canal 908. In order to mitigate this risk, system 100 preferably includes a coagulation device as discussed above. The coagulation device is preferably located on elongated member 104 because of the narrow confines of spinal canal 908. However, any coagulation device can be used provided there is enough space to accommodate the device within spinal canal 908 and the remainder of the navigated path through body 900.

Medical system 100 can also be implemented in numerous other medical procedures with or without the PIN technique. In an embodiment including suction capability, system 100 can be configured to actively circulate fluid within body 900. For instance, in the current example, saline or isotonic CSF can be introduced through member 104 into third ventricle 914 or an area adjacent to the penetration region. The excess fluid can be removed through suction member 904 and this process can be continued to provide active fluid circulation to lavage, or rinse, the cerebral ventricles or other internal portions of the body.

System 100 can be configured to perform tumor biopsies or to implant radioactive material within a tumor. System 100 can also be configured to implant electrodes within the brain or other parts of the body or can perform electrocorticography or brain stem signal recording. In addition, system 100 can be configured to induce localized hypothermia to areas of the body, in which case system 100 is configured to pump low temperature fluids through elongated member 104 to the localized region.

In one embodiment, imaging system 112 includes a magnetic resonance (MR) imaging system that allows the use of catheter 102 with external imaging in real-time. In this case, the patient is placed in MR imaging system 112 while the physician or other professional performs the navigation and tissue penetration procedures. Due to the high magnetic fields generated by MR imaging, catheter 102 preferably uses optical imaging and is substantially composed of non-magnetic or non-metallic materials that will not interfere with the MR image. Alternatively, if metallic materials are used then they can be withdrawn during the MR imaging. For instance, a metallic imager 108 can be used to navigate catheter 102 into proximity with tissue 300 and, once in place, the metallic imager 108 can be withdrawn and replaced with a non-metallic inner core 106. The penetration process can then take place using the non-metallic inner core and external MR imaging, which detects the pressure and tissue shifts within body 700 as the penetration process is performed. Other techniques, such as computed tomography (CT), computerized axial tomography (CAT) or fluoroscopy, or any combination of imaging techniques can also be used.

Figure 11:
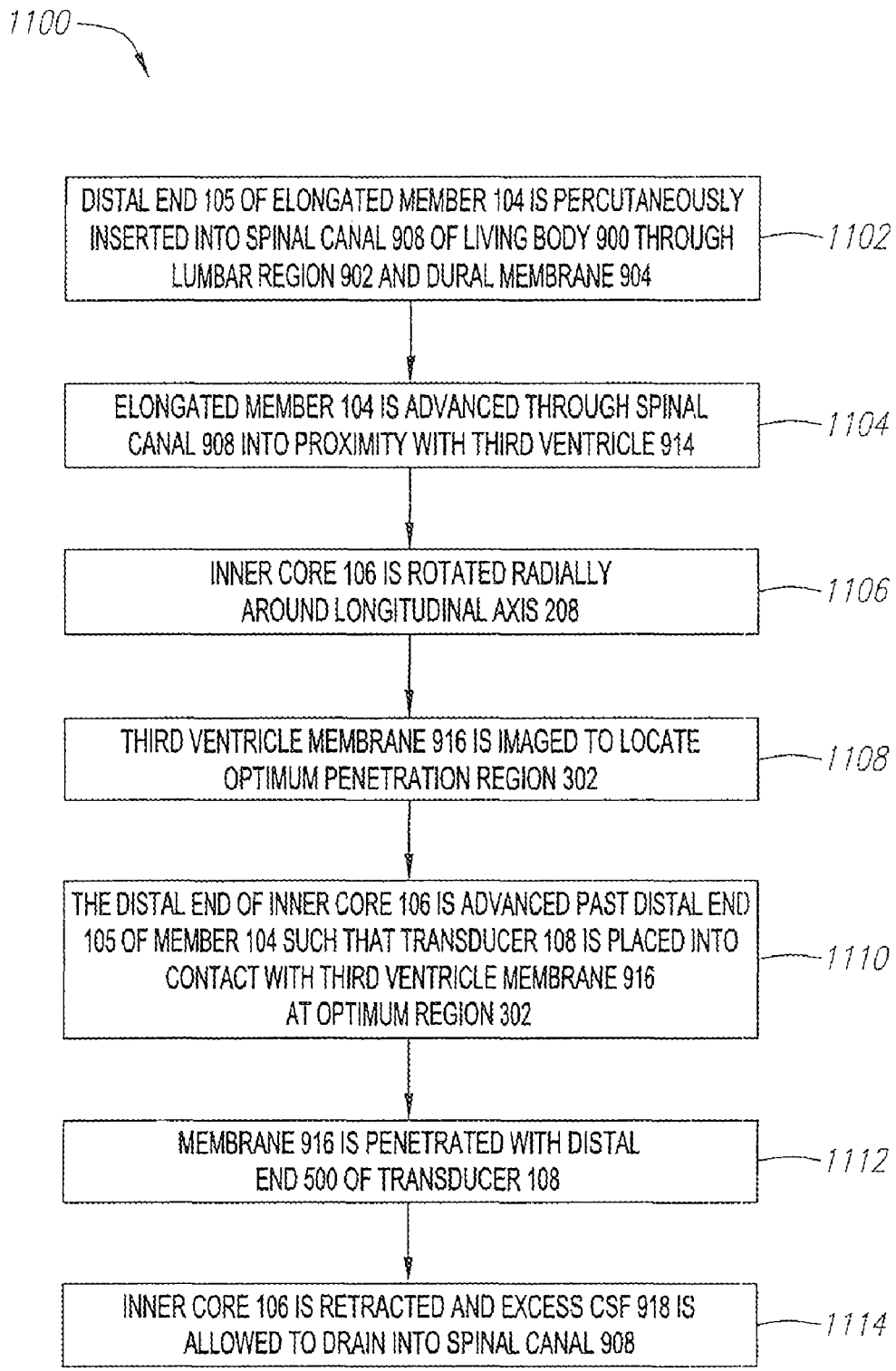
FIG. 11 is a flow diagram of another example embodiment of penetration process.

FIG. 11 depicts one embodiment of example penetration process 1100 performed within central nervous system 900. At 1102, distal end 105 of elongated member 104 is percutaneously inserted into spinal canal 908 of living body 900 through lumbar region 902 and dural membrane 904. Next at 1104, elongated member 104 is advanced through spinal canal 908 into proximity with third ventricle 914. Then, at 1106, inner core 106 is rotated radially around longitudinal axis 208 and at 1108, third ventricle membrane 916 is imaged to locate optimum penetration region 302. At 1110, the distal end of inner core 106 is advanced past distal end 105 of member 104 such that transducer 108 is placed into contact with third ventricle membrane 916 at optimum region 302. It should be noted that the rotation of inner core 106 can be initiated after it has already been advanced from within member 104, however, no imaging capability is usually available until inner core 106 begins rotating. Then, at 1112, membrane 916 is penetrated with distal end 500 of transducer 108. Finally, at 1114, inner core 106 is retracted and excess CSF 918 is allowed to drain into spinal canal 908.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. As yet another example, any kind of imaging technique may be employed, such as ultrasound, light-based (e.g., OCT or OCDR), MRI, etc. Features and processes known to those of ordinary skill may similarly be incorporated as desired. Additionally and obviously, features may be added or subtracted as desired. Accordingly, the invention is not to be restricted except in light of the attached claims and their equivalents.

What is claimed:

1. A medical system, comprising:
   a flexible inner core comprising a distal end, the distal end of the inner core comprising an imager configured to generate an image signal and to penetrate body tissue by application of axial force while being rotated;
   a flexible elongated tubular member configured to slideably receive act the inner core, the tubular member having a distal end configured to allow the inner core to advance outside the elongated member, the inner core configured to rotate radially about a longitudinal axis of the elongated member, wherein the inner core is movable between a first position where the distal end of the inner core is disposed within the tubular member, and a second position where the inner core distal end is disposed distally of the tubular member distal end;
   an imaging system communicatively coupled with the imager and configured to generate an image of the body tissue from the image signal of the imager.

2. The system of claim 1, wherein a distal end of the imager is configured to penetrate the body tissue.

3. The system of claim 2, wherein the distal end of the imager is substantially flat.

4. The system of claim 1, wherein the imaging system comprises a display configured to display the image and facilitate the location of a safe penetration region of the body tissue.

5. The system of claim 1, further comprising a control system configured to control the rotation of the inner core.

6. The system of claim 5, wherein the control system is further configured to measure a level of torque applied to the inner core.

7. The system of claim 1, wherein the elongated member is insertable into a lumen of a body.

8. The system of claim 1, further comprising a stop device configured to prevent the inner core from advancement greater than a pre-determined length past the distal end of the elongated member.

9. The system of claim 1, further comprising a gauge configured to gauge the advancement of the inner core past the distal end of the elongated member.

10. The system of claim 1, further comprising a control system coupled to a proximal end of the inner core and configured to measure a level of torque applied to the inner core when the imager penetrates the body tissue.

11. The system of claim 10, wherein the control system is further configured to control advancement of the inner core outside the elongated member and to stop advancement of the inner core when a pre-determined level of torque on the inner core is reached.

12. A medical system, comprising:
a flexible inner core comprising a distal end, the distal end of the inner core comprising an imager configured to generate an image signal, the imager having a substantially flat distal end configured to penetrate body tissue by application of axial force while being rotated;
a flexible elongated tubular member configured to slideably receive the inner core, the tubular member having a distal end configured to allow the inner core to advance outside the elongated member, the inner core configured to rotate radially about a longitudinal axis of the elongated member, wherein the inner core is movable between a first position where the distal end of the inner core is disposed within the tubular member, and a second position where the inner core distal end is disposed distally of the tubular member distal end;
an imaging system comprising a display, the imaging system communicatively coupled with the imager and configured to generate and display an image of the body tissue from the image signal of the imager; and
a control system configured to control the rotation of the inner core.

13. The system of claim 12, wherein the control system is further configured to measure a level of torque applied to the inner core.

14. A medical system, comprising:
a flexible, rotatable inner core comprising a distal end, the distal end of the inner core comprising an imager configured to generate an image signal, the imager having a distal end configured to penetrate body tissue by application of axial force while being rotated;
a flexible elongated tubular member configured to slideably receive the rotatable inner core, the tubular member having a distal end configured to allow the inner core to advance outside the elongated member, wherein the inner core is movable between a first position where the distal end of the inner core is disposed within the tubular member, and a second position where the inner core distal end is disposed distally of the tubular member distal end;
an imaging system communicatively coupled with the imager and configured to generate an image of the body tissue from the image signal of the imager; and
a control system coupled to a proximal end of the inner core and configured to measure a level of torque applied to the inner core when the imager distal end penetrates the body tissue, wherein the control system is further configured to control advancement of the inner core outside the elongated member and to stop advancement of the inner core when a pre-determined level of torque on the inner core is reached.

15. The system of claim 14, further comprising a gauge configured to gauge the advancement of the inner core past the distal end of the elongated member.

16. The system of claim 14, further comprising a stop device configured to prevent the inner core from advancement greater than a pre-determined length past the distal end of the elongated member.

* * * * *